United States Patent [19]

Levy

[11] 4,353,896

[45] Oct. 12, 1982

[54] PENETRATING TOPICAL MEDICAMENT

[76] Inventor: Michael A. Levy, 9911 Campbell, Kansas City, Mo. 64131

[21] Appl. No.: 271,427

[22] Filed: Jun. 8, 1981

[51] Int. Cl.$^3$ .............. A61K 11/56; A61K 31/60; A61K 31/605; A61K 35/78
[52] U.S. Cl. .............................. 424/195; 424/230; 424/235; 424/240; 424/331
[58] Field of Search .............. 424/230, 235, 195, 240, 424/331

[56] References Cited

U.S. PATENT DOCUMENTS

| | | | |
|---|---|---|---|
| 2,801,202 | 7/1957 | Poetsch | 424/240 |
| 2,815,315 | 12/1957 | Pottier | 424/240 |
| 2,880,130 | 3/1959 | Johnson | 424/240 |
| 2,880,138 | 3/1959 | Johnson | 424/240 |
| 2,890,152 | 6/1959 | Babcock, Jr. et al. | 424/240 |
| 3,019,162 | 1/1962 | Brunner et al. | 424/60 |
| 3,053,737 | 9/1962 | Johnson | 424/240 |
| 3,474,168 | 10/1969 | Schayer | 424/240 |
| 4,012,508 | 3/1977 | Burton | 424/235 |

OTHER PUBLICATIONS

Merck Index, 9th Ed., (1976), p. 433.

*Primary Examiner*—Stanley J. Friedman
*Attorney, Agent, or Firm*—Schmidt, Johnson, Hovey & Williams

[57] ABSTRACT

An improved topical medicament useful in treating athletic injuries or other painful subdermal conditions is provided which includes a penetrating solvent such as dimethylsulfoxide (DMSO) along with, in preferred forms, a corticosteroid (e.g., hydrocortisone acetate), a counterirritant/analgesic such as methyl salicylate, and one or more emulsifiers, a rubifacient and an alcoholic carrier. The medicaments hereof, when applied topically, are absorbed through the skin and serve to transport the corticosteroid and/or analgesic to a site of inflammation. The preferred salicylate component is converted to the analgesic salicyic acid and active metabolites in the bloodstream to serve as a pain killing agent (i.e., a prostaglandin inhibitor). The compositions hereof may be in the form of lotions, creams or aerosols, depending upon desired end use.

10 Claims, No Drawings

PENETRATING TOPICAL MEDICAMENT

BACKGROUND OF THE INVENTION

1. Field of the Invention

The present invention is concerned with greatly improved topical medicaments which can penetrate the skin and transport an anti-inflammatory corticosteroid and/or an analgesic to enhance the effectiveness of such components. More particularly, it is concerned with such topical medicaments which include a penetrating solvent such as dimethylsulfoxide (DMSO) or an alcohol along with a corticosteroid and/or a counterirritant-/analgesic, and, preferably, a rubefacient, one or more suspending agents (e.g., emulsifiers), and a carrier.

2. Description of the Prior Art

Corticosteroids such as the hydrocortisones and their various derivatives are known to be useful medicinal agents. For example, these substances can be applied topically for the purpose of treatment of dermatoses of various types. These materials are known to have anti-inflammatory, antipruritic and vasoconstrictive actions. The clinical efficacy of topical corticosteroids is dependent upon the extent of percutaneous absorption or penetration of the active drug through the skin. Factors influencing absorption include the agent used, the concentration of the drug, the vehicle used, and the anatomical site of application. Topically applied corticosteroid preparations are available in nonprescription form for the temporary relief of minor skin irritations, itching and rashes due to eczema, dermatitis, insect bites, poison ivy, poison oak, poison sumac, soaps, detergents, cosmetics, jewelry and itchy genital and anal areas.

In addition, corticosteroids have been prepared in injectable form for treatment of inflamed body parts such as knees or other joints. To give but one example, these preparations can be injected for the treatment of painful athletic injuries such as knee sprains and the like.

Dimethylsulfoxide (DMSO) is an extraordinary chemical in the form of a highly polar, stable, hygroscopic organic liquid with exceptional solvent properties. Its industrial applications are numerous and diverse, being used as a solvent for resins, fungicides, dyes, pigments etc., as a reactant for chemical synthesis, as an extractant, and as a reaction medium to accelerate rates of chemical combination.

DMSO has also been tested for use in certain types of topical preparations, e.g., see "Topical Pharmacology and Toxicology of Dimethyl Sulfoxide—Part I," *Journal of the American Medical Association,* Vol. 193, No. 10, p. 796, and literature cited therein.

Counterirritants are sometimes employed in topical medicaments for the symptomatic relief of pain. Counterirritants are agents that are applied locally to produce an inflammatory reaction with the object of affecting another site usually adjacent to or underlying the surface irritated. The intensity of response of the skin depends on not only the nature of the irritant employed, but also its concentration, the solvent in which it is dissolved, and the period of contact. A counterirritant drug is typically applied to the skin where pain is experienced. Pain is only as intense as it is perceived, and the perception of other sensations from the application of the counterirritant, such as massage and warmth, tend to crowd out perception of the pain. In addition, such products may produce an increase in the flow of blood to the muscles which, with concomitant waste disposal and other chemical changes, enhances recovery. Various types of counterirritants have been employed in the past, e.g., methyl salicylate, camphor, menthol, eugenol, eucalyptol and thymol.

Additional background patents and literature references in connection with the instant invention include:
U.S. Pat. No. 2,801,202—Compositions Containing Cortisone or Hydro-Cortisone with Phenylephrine
U.S. Pat. No. 2,815,315—Analgesic and Antirheumatic Preparation
U.S. Pat. No. 2,880,130—Anti-inflammatory Steroid Solutions
U.S. Pat. No. 2,880,138—Anti-inflammatory Steroid Solutions
U.S. Pat. No. 2,890,152—Topical Anti-inflammatory Compositions
U.S. Pat. No. 3,019,162—Cinchophen-Hydrocortisone Topical Compositions
U.S. Pat. No. 3,053,737—N-Acetyl-p-Aminophenol Anti-inflammatory Steroid Compositions
U.S. Pat. No. 3,474,168—Prevention of Corticosteroid Side Effects
U.S. Pat. No. 4,012,508—Topical Composition and Method
"Rubs and Liniments," *Facts and Comparisons,* pp. 1653–1655 (1981)
"Emulsifying and Suspending Agents," *Pharmaceutical Necessities—Remingtons Pharmaceutical Science,* Chapter 64, pp. 1244–1253 (1980)
"Emulsions," *Particle Phenomena and Coarse Dispersions—Remingtons Pharmaceutical Science*
"Hormones," *Remingtons Pharmaceutical Science,* 16th Ed., pp. 901–912 (1980)
"Corticosteroids, Topical," *Fact & Comparisons,* pp. 1620–1628 (1981)

SUMMARY OF THE INVENTION

The present invention provides a greatly improved topical medicament which includes a member selected from thep group consisting of the corticosteroids, derivatives of the corticosteroids, and mixtures thereof, a substance selected from the group consisting of methyl salicylate, triethanolamine salicylate, salicyamide, oil of eucalyptus, menthol and mixtures thereof, and an amount of a penetrating solvent such as DMSO or a lower alcohol (i.e., an alcohol having from 1-4 carbon atoms, inclusive). A medicament of this type is particularly useful for the topical treatment of sprains or other types of athletic injuries. In use, the penetrating solvent serves to transport at least the corticosteroid component to a subcutaneous site of inflammation in order to reduce and ameliorate the effects thereof. At the same time, the counterirritant substance serves to lessen the pain and discomfort commonly experienced with such athletic injuries, and serves to increase blood flow. In particularly preferred forms, the counterirritant substance is selected from the group consisting of methyl salicylate, triethanolamine salicylate, and salicyamide. These materials are converted to salicyclic acid in the bloodstream, and in this form serve as effective pain killers.

The topical medicament hereof can be in various forms such as lotions, creams, jellies or aerosols. Depending upon the desired form, the medicament may include one or more suspending agents such as sodium lauryl sulfate, stearyl alcohol, cetyl alcohol, glycerol monostearate, the polyethylene glycols, bentonite, tragacanth, and mixtures thereof. In the case of a lotion product for example, a plurality of emulsifiers may be employed.

DESCRIPTION OF THE PREFERRED EMBODIMENTS

As noted above, the medicaments of the present invention include a corticosteroid or derivative thereof, and most preferably a member selected from the group consisting of the hydrocortisones and derivatives thereof, with hydrocortisone acetate being a typical example. This component is preferably present at a level of up to about 10% by volume in the final medicament, and more preferably from about 0.5 to 5% by volume, and most preferably about 0.5% by volume.

The counterirritant/analgesic substance is preferably present at a level of up to about 50% by volume, more preferably from about 10 to 35% by volume, and most preferably about 15% by volume. On the other hand, the solvent component is advantageously used at a level of from about 5 to 90% by volume, more preferably from about 5 to 50% by volume, and most preferably about 15% by volume.

Although the amounts of suspending agents may vary depending upon desired characteristics in the final medicament, as a general rule the total amount of suspending agent should be present at a level of up to about 15% by volume.

In certain compositions in accordance with the invention, the medicament may include a rubefacient such as camphor, normally at a level of up to about 5% by volume.

The following table sets forth preferred components useful in the preparation of a lotion-type topical medicament in accordance with the invention. The ranges of use of the respective components are set forth, along with the most preferred amounts:

TABLE

| Component | Usual Ranges (Vol. %) | Most Preferred (Vol. %) |
| --- | --- | --- |
| DMSO | 5–90 | 15 |
| Hydrocortisone acetate | 0–10 | 0.5 |
| Methyl salicylate | 0–50 | 15 |
| Camphor | 0–5 | — |
| Cetyl alcohol | 0–4 | 0.5 |
| Stearyl alcohol | 0–4 | 0.5 |
| Glycerol monostearate | 0–6 | 1 |
| Menthol | 0–5 | — |
| Isopropyl alcohol | 0–50% | 10 |
| Distilled Water | 0–80% | 57.5 |
|  |  | 100.0 |

In preparative procedures using the most preferred components in the foregoing Table, an aqueous phase is formulated by adding the glycerol monostearate to 50% distilled water, followed by heating until the monostearate is dissolved and a homogenous mixture results. The aqueous phase is then allowed to cool. An oleaginous phase is next prepared by adding the hydrocortisone to isopropyl alchol, with gentle stirring to dissolve the hydrocortisone. The DMSO is next added to the methy salicylate, again with gentle stirring. The hydrocortisone/alcohol and DMSO/methyl salicylate mixtures are then blended together, and the cetyl and stearyl alcohol are added thereto. The entire mixture is then heated until all components are fully dissolved.

The oleaginous phase is slowly added to the cooled aqueous phase, with vigorous stirring (e.g., using an electric stirrer or Hobart mixer), whereupon the remaining 7.5% distilled water is added with stirring until a uniform emulsion has been obtained.

In the use of a lotion-type composition as described, the medicament is simply applied to the skin at the region of pain. For example, in the case of a knee sprain, the lotion is applied on the skin adjacent the affected knee. The DMSO or alcoholic solvent serves to transport the hydrocortisone component to a subcutaneous site for treatment of inflammation, whereas the methyl salicylate and other components (if used) serve as counterirritants or rubifacients in order to lessen pain. The methyl salicylate is transported subcutaneously and is converted in the bloodstream to the analgesic salicylic acid. This also serves to kill the pain associated with the injury.

I claim:

1. A penetrating topical medicament, comprising:
    from about 0.5 to 5% by volume of a member selected from the group consisting of the corticosteroids, derivatives of the corticosteroids, and mixtures thereof;
    from about 10 to 35% by volume of a substance selected from the group consisting of methyl salicylate, triethanolamine salicylate, salicyamide, oil of eucalyptus menthol and mixtures thereof; and
    from about 5 to 50% by volume of a medium for transporting said at least said member through the skin to a subcutaneous site.

2. The medicament as set forth in claim 1, including an agent selected from the group consisting of sodium lauryl sulfate, stearyl alcohol, cetyl alcohol, glycerol monostearate, polyethylene glycol, bentonite, tragacanth, and mixtures thereof.

3. The medicament as set forth in claim 1, said agent being present at a level of up to about 15% by volume.

4. The medicament as set forth in claim 1, including a rubefacient.

5. The medicament as set forth in claim 4, said rubefacient being camphor.

6. The medicament as set forth in claim 4, said rubefacient being present at a level of up to about 5% by volume.

7. The medicament as set forth in claim 1, said member being selected from the group consisting of hydrocortisone and derivatives thereof.

8. The medicament as set forth in claim 1, said medium being dimethyl sulfoxide.

9. The medicament as set forth in claim 1, said medium being a lower alcohol.

10. A penetrating topical medicament, comprising:
    from about 5 to 90% by volume of dimethyl sulfoxide; and
    from about 10 to 35% by volume of a member selected from the group consisting of methyl salicylate, triethanolamine salicylate, salicyamide and mixtures thereof.

* * * * *